United States Patent
Brunner et al.

(10) Patent No.: US 6,950,183 B2
(45) Date of Patent: Sep. 27, 2005

(54) APPARATUS AND METHOD FOR INSPECTION OF PHOTOLITHOGRAPHIC MASK

(75) Inventors: Timothy A. Brunner, Ridgefield, CT (US); Michael S. Hibbs, Westford, VT (US); Christopher J. Progler, Plano, TX (US)

(73) Assignee: International Business Machines Corporation, Armonk, NY (US)

( * ) Notice: Subject to any disclaimer, the term of this patent is extended or adjusted under 35 U.S.C. 154(b) by 236 days.

(21) Appl. No.: 10/248,808

(22) Filed: Feb. 20, 2003

(65) Prior Publication Data

US 2004/0165182 A1 Aug. 26, 2004

(51) Int. Cl.[7] .............................................. G01N 21/88
(52) U.S. Cl. .................................... 356/237.5; 356/394
(58) Field of Search ............................ 356/237.4, 237.5, 356/394; 382/144

(56) References Cited

U.S. PATENT DOCUMENTS

| | | |
|---|---|---|
| 4,555,798 A | 11/1985 | Broadbent, Jr. et al. |
| 4,641,353 A | 2/1987 | Kobayashi |
| 5,162,867 A | 11/1992 | Kohno |
| 5,481,624 A | 1/1996 | Kamon |
| 6,023,328 A * | 2/2000 | Pierrat ..................... 356/237.4 |
| 6,268,093 B1 | 7/2001 | Kenan et al. |
| 6,800,421 B2 * | 10/2004 | Hasegawa et al. .......... 430/311 |

FOREIGN PATENT DOCUMENTS

| | | |
|---|---|---|
| JP | 7175205 A | 7/1995 |
| JP | 9211840 A | 8/1997 |

* cited by examiner

Primary Examiner—Richard A. Rosenberger
(74) Attorney, Agent, or Firm—DeLio & Peterson, LLC; Peter W. Peterson; Todd M. C. Li

(57) ABSTRACT

A method for inspecting masks used to project patterns in photolithographic imaging comprises initially providing a photolithographic mask having a pattern field thereon, where in normal production use the pattern is transferred by a reduction projector as a demagnified pattern on a production substrate, and providing a movable field-defining aperture adjacent the mask, the aperture having a field area less than, and capable of defining a pattern subfield comprising only a portion of the entire photolithographic mask pattern field. The method then includes aligning the field-defining aperture with a pattern subfield comprising only a portion of the entire photolithographic mask pattern field. Using an energy source, the method includes projecting the pattern subfield onto a test substrate and exposing onto the test substrate the pattern subfield at a size between that normally exposed on a production substrate and the actual size of the pattern subfield on the photolithographic mask. Subsequently, the method includes inspecting the exposed pattern subfield on the test substrate for defects in the photolithographic mask.

15 Claims, 1 Drawing Sheet

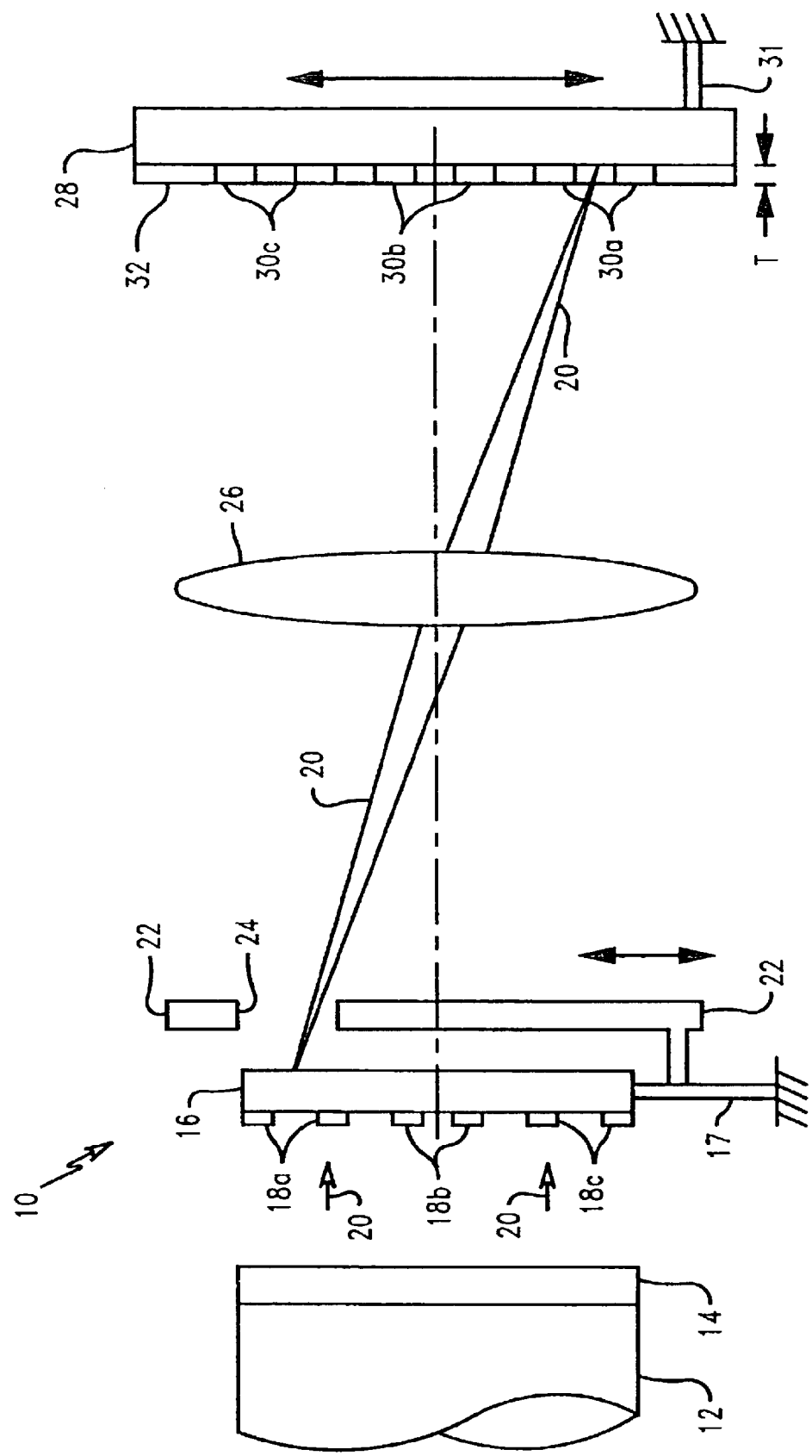

APPARATUS AND METHOD FOR INSPECTION OF PHOTOLITHOGRAPHIC MASK

BACKGROUND OF INVENTION

1. Field of the Invention

This invention relates to lithographic processing of microelectronics products and, in particular, to a method and system for inspecting masks used to project patterns in photolithographic imaging.

2. Description of Related Art

In manufacturing integrated circuits, it is a goal to build a defect-free photomask with the desired patterns, which then are projected and exposed onto the resist layers on a wafer during lithographic processing to create the circuits. Inspecting the photomasks is becoming more difficult because the mask patterns are becoming smaller. A variety of resolution enhancement technologies such as sub-resolution assist features, optical proximity correction and phase shift mask approaches may be used, and each of these has inspection issues. While the wavelength of the energy source used in the exposure tool continues to decrease, the wavelength of the energy source used in the inspection tool is lagging behind. Currently, the industry typically uses inspection tools with a light wavelength of 365 nm to inspect masks intended for exposure tools employing a light wavelength of 193 nm.

Some believe that an ideal mask inspection would be done with the same wavelength of the energy or radiation used in the exposure tool, and using exactly the same diffraction orders as the stepper. The AIMS system, invented by IBM Corporation and commercially available from Zeiss, can perform such an actinic inspection. However, it would be desirable to be able to completely inspect a mask in less time than that taken by the AIMS system. For certain attenuated phase shift masks (PSM), the lack of actinic inspection presents problems. For example, a 193 nm attenuated PSM is fairly transparent at the 365 nm inspection wavelength, which reduces signal contrast and makes inspection problematic. U.S. Pat. No. 6,023,328 discloses a method of inspecting a photomask by magnifying the image on a test substrate to a size larger than that on the mask. However, this patent does not disclose or suggest the manner in which specific fields may be exposed or how to optimize the resist layer on the test substrate.

SUMMARY OF INVENTION

Bearing in mind the problems and deficiencies of the prior art, it is therefore an object of the present invention to provide an improved method and apparatus for inspecting photomasks having small pattern feature sizes using light wavelengths which are greater than those used during circuit production.

It is another object of the present invention to provide a method and apparatus which reduces the time heeded for inspecting photomasks.

A further object of the invention is to provide a method and apparatus for inspecting photomasks which utilizes an intermediate test substrate with a transferred pattern which is easily inspected.

It is another object of the present invention to provide a photomask inspection method and apparatus which achieves high contrast, and thus easy inspection, by optimizing the film properties of the test substrate, such as the resist thickness.

It is yet another object of the present invention to provide a method and apparatus for inspecting photomasks which improves the detection of printable defects.

The above and other objects and advantages, which will be apparent to one of skill in the art, are achieved in the present invention which is directed to, in a first aspect, a method for inspecting masks used to project patterns in photolithographic imaging. The method comprises initially providing a photolithographic mask having a pattern field thereon, where in normal production use the pattern is transferred by a reduction projector as a demagnified pattern on a production substrate, and providing a movable field-defining aperture adjacent the mask, the aperture having a field area less than, and capable of defining a pattern subfield comprising only a portion of, the entire photolithographic mask pattern field. There is also providing an energy source and a test substrate sensitive to energy from the source. The method then includes aligning the field-defining aperture with a pattern subfield comprising only a portion of the entire photolithographic mask pattern field. Using the energy source, the method includes projecting the pattern subfield onto the test substrate and exposing onto the test substrate the pattern subfield at a size between that normally exposed on a production substrate and the actual size of the pattern subfield on the photolithographic mask. Subsequently, the method includes inspecting the exposed pattern subfield on the test substrate for defects in the photolithographic mask.

Preferably, the portion of the photolithographic mask pattern field is exposed onto the test substrate at a size between about one-half the actual size of the pattern subfield portion and the actual size of the pattern subfield on the photolithographic mask.

The method may further include repeatedly aligning the field-defining aperture with different pattern subfields comprising different portions of the entire photolithographic mask pattern field, projecting the different pattern subfields onto the substrate and exposing onto the substrate the different pattern subfields at a size between that normally exposed in lithographic imaging production and the actual size of the pattern subfields. Preferably, during the repeated alignment of the field-defining aperture with different pattern subfields, the pattern subfields are partially overlapped with at least one portion of a pattern subfield previously exposed onto the test substrate.

The method may further include repeatedly projecting the pattern subfield onto different areas of the test substrate and exposing onto the test substrate a plurality of the same pattern subfields at a size between that normally exposed in lithographic imaging production and the actual size of the pattern subfield. During inspection of the exposed portion of the pattern subfield on the test substrate, the repeated, same pattern subfields are compared with each other to distinguish repeated defects in the mask from random defects on the test substrate.

The method may also include repeatedly projecting the pattern subfield onto different areas of the test substrate and exposing onto the test substrate a plurality of the same pattern subfields at different focus values and at a size between that normally exposed in lithographic imaging production and the actual size of the pattern subfield.

Preferably, the exposed pattern subfield inspected on the test substrate is smaller than the pattern subfield on the photolithographic mask, and is centered substantially within the exposed pattern subfield.

The energy source may project energy at a wavelength equal to or less than that normally used with the photolithographic mask in lithographic imaging production, or at a wavelength greater than that normally used with the photolithographic mask in lithographic imaging production. Preferably, the energy source of the inspection projector has the same wavelength as, and mimics, the energy source used in normal production.

The test substrate preferably includes a layer of resist material sensitive to energy from the source, and the resist layer has a thickness of about $m\lambda/(4n)$, wherein m is an odd integer, n is the refractive index of the resist material, and I is the wavelength of an energy source used in the inspection.

The projecting of the pattern subfield onto the test substrate is preferably performed using an inspection projector and wherein the inspecting of the exposed pattern subfield on the test substrate for defects in the photolithographic mask is performed using a high speed inspection tool.

In another aspect, the present invention is directed to an apparatus for inspecting masks used to project patterns in photolithographic imaging comprising an energy source a substrate sensitive to energy from the source, a mask fixture, and a photolithographic mask having a pattern field thereon mounted on the fixture and disposed between the energy source and the substrate, the pattern field being normally exposed in lithographic imaging production to a size less than that on the mask. The apparatus also includes a movable field-defining aperture having a designated field area less than the photolithographic mask pattern field, aligned with a portion of the photolithographic mask pattern field, disposed between the energy source and the substrate, the designated field-defining aperture area being movable to align with different portions of the photolithographic mask pattern field. The apparatus further includes a lens system between the photolithographic mask and the substrate adapted to project the portion of the photolithographic mask pattern field aligned with the field-defining aperture onto the substrate and exposing onto the substrate the portion of the photolithographic mask pattern field at a reduction between about 2 times and 0.5 times the actual size of the portion of the photolithographic mask pattern field.

BRIEF DESCRIPTION OF DRAWINGS

The features of the invention believed to be novel and the elements characteristic of the invention are set forth with particularity in the appended claims. The figures are, for illustration purposes only and are not drawn to scale. The invention itself, however, both as to organization and method of operation, may best be understood by reference to the detailed description which follows taken in conjunction with the accompanying drawings in which:

The FIGURE is a schematic illustration of an example of the actinic mask projector of the present invention used to create the wafers which test the photolithographic masks.

DETAILED DESCRIPTION
Description of the Preferred Embodiment(s)

In describing the preferred embodiment of the present invention, reference will be made herein to the FIGURE of the drawings in which like numerals refer to like features of the invention. Features of the invention are not necessarily shown to scale in the drawings.

The present invention describes a solution to prior problems of inspecting a photomask used in lithographic processing of microelectronic circuits. The present invention comprises a system combining: (1) an actinic inspection projector, i.e., one using the same radiation wavelength as the production stepper, to create photolithographic images of the mask patterns on a test wafer and (2) an inspection system that uses a radiation source of higher wavelength to inspect the pattern images created on the test wafer.

A preferred actinic inspection projector system 10 is shown in the FIGURE, where an energy or radiation source 12 is coupled to an aperture control 14 and emits radiation 20 of a desired wavelength. Typically, such radiation is light at a wavelength of 248 nm, 193 nm or 157 nm, or even lower 13nm extreme ultra violet (EUV) wavelengths, or even electron or other particle beam exposure. Photolithographic mask 16 is used to project patterns in photolithographic imaging, and is to be tested in accordance with the method of the present invention. Standard mask sizes are about 6 in. (150 mm) square. As shown, mask 16 contains subfields of the same or different patterns 18a, 18b, 18c printed thereon, typically with opaque chrome lines on a transparent quartz substrate. Photolithographic mask 16 is held by fixture 17. As shown in the FIGURE, radiation 20 passes through mask pattern 18a and is inverted by reduction objective lens 26 and projected onto test wafer or other test substrate 28 having a layer of resist material 32. Wafer 30 is mounted to a work piece holder 31 which is movable in the direction indicated by the arrow. While the wafer may be of any size, a 200 mm diameter wafers is an economical, industry-standard format. The mask pattern 18a creates a latent image of the pattern 30a in the resist layer. These latent images may then be developed and etched by well-known processes.

The method of the present invention utilizes a magnification that permits the patterns created on the wafer to be easily inspected. Typically a 4× reduction lens is used in the production stepper to create the images on the wafers, but this reduction creates features too small to inspect easily. Preferably, a 1× reduction lens, i.e., a lens that creates an image the same size as the mask pattern, is employed to produce features on the mask inspection wafer four times larger than the production wafer, and would be much more inspectable. An additional advantage of 1× optics is that other particularly symmetric, simple 1× optical systems may be employed, such as the Offner mirror system or the Wynne-Dyson system. Mirror systems are particularly attractive since they are inherently achromatic and might be used at more than one exposure wavelength, e.g. SVGL Model 600 Micralign machine. While a 1× reduction magnification is employed in the preferred embodiment, other reduction ratios may be employed, between 2× (i.e., half mask size) and 0.5× (twice mask size).

In describing a preferred embodiment of the present invention, the photomasks used for wafer production and to be inspected are employed in, for example, a 193 nm wavelength production exposure system using 4× reduction optics with a wafer side numerical aperture equal to 0.8 (0.8 NA) and a partial coherence value of 0.85. The NA is the sine of the most oblique (largest) angle allowed by the optical system. For this example it is preferred that the mask exposure system of the present invention use a light wavelength 193 nm and a 1× reduction optics system adjusted to 0.2 NA (which would match the NA on the reticle side of the production stepper), with the illumination adjusted to 0.85 partial coherence. In this manner the 1× mask projector would form images using precisely the same diffraction orders as the production stepper. If the 1× projection optics has 0.25 NA (i.e., the same on both sides of the optics), and a variable aperture to choose lower NA, then a perfect match can be made to any 4× production optics with any NA, up to and including 1 NA. Even if an immersion lens is used such that the effective NA is greater than 1, e.g., 1.3, then a modest NA 1× projection lens will suffice, e.g. NA=1.3/4= 0.325.

The mask projector system of the present invention preferably has a field size smaller than the full photomask, to break the exposure up into smaller segments. One solution is to use the SVCL Micralign full field approach where a ring-shaped field sweeps out the full image. While this design is limited to a 0.166 NA, higher numerical aperture values are possible. In the present method, a modest pattern field size of, for example, 10 mm on a side, may be employed. As shown in the FIGURE, the mask 16 under test is mounted adjacent to movable field-defining aperture 22, having an opening 24 of the example 1 cm2 pattern field size which may be moved to any desired part of the mask. Opening 24 may be of any desired size or configuration, preferably square or rectangular, and is movable to any desired portion of the entire photolithographc mask pattern field. As a result of the particular orientation shown, pattern field 18a is then printed by the 1× optics 26 as pattern 30a on test wafer 28. Aperture opening 24 may then be subsequently moved to different areas of mask 16, to print pattern field 18b as wafer image 30b, and pattern field 18c as wafer image 30c. To test a 6" mask having a 120 mm square pattern field, 144 separate subfields would be required to be printed onto the wafer. In order to avoid testing critical patterns portions at the edges of these fields, it is preferable to print a slightly larger field, e.g., 10.5 mm on a side, but only inspect the center 10 mm square. Also, by moving the wafer position, each subfield of the mask may be printed onto the wafer a plurality of times. Thus, in the FIGURE images 30a, 30b and 30c on wafer 28 may represent repeated printing of the same subfield pattern 18a. This would permit detection of repeatable defects from the mask, with random wafer processing defects excluded. Further, each subfield may be printed at different values of focus and then inspected to insure that the mask patterns printed properly over a desired depth of focus. Printing of different focus values would also permit printing of certain phase shift defects. To print all subfields of a 6" test mask would typically require several wafers, but the relatively high throughput of a system such as that shown in the FIGURE would make it possible to expose and develop these wafers in a relatively short time.

The method of the present invention may be used to inspect the pattern image on the wafer as either a latent image, a developed image, or as an etched image. It is preferred that the image be developed for the inspection process, which may be performed by a high speed inspection tool, similar to a KLA AIT XP inspection tool. Either die-to-die or die-to-database modes might be used depending on the periodicity of the mask patterns. A suitable inspection tool is available from KLA-Tencor Corporation of San Jose, Calif.

The present invention also includes optimizing the resist process for high contrast at the inspection wavelength. The resist layer preferably has a thickness T (see FIGURE) in accordance with the following equation:

$$T \approx m\lambda/(4n)$$

wherein m is an odd integer, $\lambda$ is the wavelength of an energy source used in the inspection, and n is the refractive index of the resist material.

Currently, state-of-the-art inspection tools use 365 nm light. On bare silicon, a resist having a refractive index of 1.5 would result in a thickness T of approximately 60 nm, which would give good contrast relative to the bare silicon. The resist pattern produced on the test wafer would be four times larger than that on the desired production wafer, since a 1× reduction is employed mask test projection instead of the 4× reduction in the production stepper. Therefore all the resolution enhancement technology, such as use of phase shift masks, sub-resolution assist features, and optical proximity correction (OPC), has been applied to this pattern under test. For example, sub-resolution assist features will not print, but any "printable" defect due to the assist features will print. If used in a die-to-database mode, it is important to note that the appropriate database would be the actual pattern to be printed on the wafer, not the pattern on the mask with assists and various OPC modification. The 1× test wafer would be useful for verifying OPC effectiveness and measuring sources of systematic line width variation.

Thus, the preferred embodiment of the present invention comprises a two step inspection method where first wafers are printed using a 1× reduction stepper with its numerical aperture adjusted to correspond to the desired 4× reduction production stepper, and then a modified KLA die-to-database inspection machine is used to examine the wafer. The KLA inspection machine may be optimized to inspect the pattern on the test substrate, for example, by using a resist pattern on silicon wafers. The present invention cleanly separates out the actinic projector from the inspection tool. As lithography technologies continue to evolve from 248 nm to 193 nm to 157 nm to EUV wavelengths or particle beam lithography, only the actinic projector need change. Since the 1× actinic stepper itself has a low numerical aperture, it is relatively easy to build compared to the high numerical aperture production stepper. The inspection optics itself may use whatever wavelength and optics is adequate for inspecting the wafer patterns. The present invention completely avoids the considerable problem of changing the light source and optics and detectors of the inspection tool itself which have prevented inspection tools from keeping up with wavelength changes of lithography tool.

The present invention permits inspection of separate subfields of patterns similar to those printed on product wafers, but larger. This achieves completely ideal AIMS-like inspection capability without using actinic inspection optics, and has excellent extendability as production wavelengths decrease. It may be employed in electron-beam projection lithography, EUV lithography, or any lithography which utilizes masks. Thus, all of the advantages of an AIMS-like inspection can be achieved using standard high-speed (non-AIMS) inspection tools.

While the present invention has been particularly described, in conjunction with a specific preferred embodiment, it is evident that many alternatives, modifications and variations will be apparent to those skilled in the art in light of the foregoing description. It is therefore contemplated that the appended claims will embrace any such alternatives, modifications and variations as falling within the true scope and spirit of the present invention.

What is claimed is:

1. A method for inspecting masks used to project patterns in photolithographic imaging comprising:

providing a photolithographic mask having a pattern field thereon, where in normal production use the pattern is transferred by a reduction projector as a demagnified pattern on a production substrate;

providing a movable field-defining aperture adjacent the mask, the aperture having a field area less than, and capable of defining a pattern subfield comprising only a portion of, the entire photolithographic mask pattern field;

providing an energy source and a test substrate sensitive to energy from the source;

aligning the field-defining aperture with a pattern subfield comprising only a portion of the entire photolithographic mask pattern field;

using the energy source, projecting the pattern subfield onto the test substrate and exposing onto the test substrate the pattern subfield at a size between that normally exposed on a production substrate and the actual size of the pattern subfield on the photolithographic mask; and inspecting the exposed pattern subfield on the test substrate for defects in the photolithographic mask.

2. The method of claim 1 wherein the portion of the photolithographic mask pattern field is exposed onto the test substrate at a size between about one-half the actual size of the pattern subfield portion and the actual size of the pattern subfield on the photolithographic mask.

3. The method of claim 1 further including repeatedly aligning the field-defining aperture with different pattern subfields comprising different portions of the entire photolithographic mask pattern field, projecting the different pattern subfields onto the substrate and exposing onto the substrate the different pattern subfields at a size between that normally exposed in lithographic imaging production and the actual size of the pattern subfields.

4. The method of claim 3 wherein during the repeated alignment of the field-defining aperture with different pattern subfields, the pattern subfields are partially overlapped with at least one portion of a pattern subfield previously exposed onto the test substrate.

5. The method of claim 1 further including repeatedly projecting the pattern subfield onto different areas of the test substrate and exposing onto the test substrate a plurality of the same pattern subfields at a size between that normally exposed in lithographic imaging production and the actual size of the pattern subfield.

6. The method of claim 5 wherein during inspection of the exposed portion of the pattern subfield on the test substrate, the repeated, same pattern subfields are compared with each other to distinguish repeated defects in the mask from random defects on the test substrate.

7. The method of claim 1 further including repeatedly projecting the pattern subfield onto different areas of the test substrate and exposing onto the test substrate a plurality of the same pattern subfields at different focus values and at a size between that normally exposed in lithographic imaging production and the actual size of the pattern subfield.

8. The method of claim 1 wherein the exposed pattern subfield inspected on the test substrate is smaller than the pattern subfield on the photolithographic mask.

9. The method of claim 1 wherein the exposed pattern subfield inspected on the test substrate is smaller than and centered substantially within the exposed pattern subfield.

10. The method of claim 1 wherein the energy source projects energy at a wavelength equal to or less than that normally used with the photolithographic mask in lithographic imaging production.

11. The method of claim 1 wherein the inspection is performed with an energy source having a wavelength greater than that normally used with the photolithographic mask in lithographic imaging production.

12. The method of claim 1 wherein the test substrate includes a layer of resist material sensitive to energy from the source, and the resist layer has a thickness of about $m\lambda/(4n)$ wherein m is an odd integer, n is the refractive index of the resist material, and $\lambda$ is the wavelength of an energy source used in the inspection.

13. The method of claim 1 wherein the projecting of the pattern subfield onto the test substrate is performed using an actinic inspection projector and wherein the inspecting of the exposed pattern subfield on the test substrate for defects in the photolithographic mask is performed using a high speed inspection tool.

14. An apparatus for inspecting masks used to project patterns in photolithographic imaging comprising:

an energy source;

a workpiece holder for a substrate sensitive to energy from the source;

a mask fixture;

a photolithographic mask having a pattern field thereon mounted on the fixture and disposed between the energy source and the substrate, the pattern field being normally exposed in lithographic imaging production to a size less than that on the mask;

a movable field-defining aperture having a designated field area less than the photolithographic mask pattern field, aligned with a portion of the photolithographic mask pattern field, disposed between the energy source and the substrate, the designated field-defining aperture area being movable to align with different portions of the photolithographic mask pattern field; and a lens system between the photolithographic mask and the substrate adapted to project the portion of the photolithographic mask pattern field aligned with the field-defining aperture onto the substrate and exposing onto the substrate the portion of the photolithographic mask pattern field at a reduction between about 2 times and 0.5 times the actual size of the portion of the photolithographic mask pattern field.

15. The apparatus of claim 14 wherein the lens system has a reduction between about 1 time and 0.5 times the actual size of the portion of the photolithographic mask pattern field.

* * * * *